United States Patent

Stanley et al.

[11] Patent Number: 6,162,468
[45] Date of Patent: Dec. 19, 2000

[54] FROZEN AQUEOUS SOLUTION WITH NUTRIENTS METHOD OF PACKAGING AND UTILIZING THE SAME

[75] Inventors: Steven A. Stanley, Plantation; John A. Pachivus, North Miami; John R. Annis, Sunrise, all of Fla.

[73] Assignee: Med Tech Industries, Inc., Hollywood, Fla.

[21] Appl. No.: 09/369,123

[22] Filed: Aug. 5, 1999

[51] Int. Cl.[7] .................. A61K 31/595; A61K 31/44; A61K 31/355; A61K 31/34; A61K 31/07; A61K 33/00; A61K 33/32; A61K 33/26; A61K 33/36; A61K 31/70

[52] U.S. Cl. ................. 424/600; 424/643; 424/646; 424/667; 514/52; 514/168; 514/351; 514/356; 514/458; 514/474; 514/725

[58] Field of Search ................... 424/600, 643, 424/646, 667; 514/52, 168, 351, 458, 474, 725, 356

[56] References Cited

U.S. PATENT DOCUMENTS

| | | | |
|---|---|---|---|
| 4,021,583 | 5/1977 | Arden | 426/134 |
| 4,218,482 | 8/1980 | Cook et al. | 426/72 |
| 4,293,578 | 10/1981 | Stone | 426/66 |
| 4,537,194 | 8/1985 | Hanson et al. | 128/399 |
| 4,992,282 | 2/1991 | Mehansho et al. | 426/72 |
| 5,431,915 | 7/1995 | Harvey et al. | 424/439 |
| 5,698,247 | 12/1997 | Hall | 426/66 |
| 5,780,451 | 7/1998 | DeMichele et al. | 514/54 |
| 5,840,057 | 11/1998 | Aloisi | 604/20 |

OTHER PUBLICATIONS

Handbook of Nonprescription Drugs, 8th edition, pp. 338–339, 1986.

Ross Products Division, Abbott Laboratories, Inc. "Diarrhea can be Dangerous", 1998, middle panel "Freezer Pops" (1998).

Primary Examiner—Raymond Henley, III
Attorney, Agent, or Firm—Malin, Haley & DiMaggio, P.A.

[57] ABSTRACT

The invention encompasses a frozen composition containing an active ingredient. The active ingredients include but are not limited to a nutrient mixture and a medicine. In its preferred embodiment, the chemical composition contains the following ingredients: a nutrient mixture, at least one flavoring agent, preservatives, food coloring, and a balance of water. The composition can be placed in a sealed plastic bag and frozen to form a nutrient enriched ice pop. Alternatively, the composition can be frozen in-situ, either with or without a stick inserted therein. The invention also includes methods of consuming the composition.

7 Claims, 1 Drawing Sheet

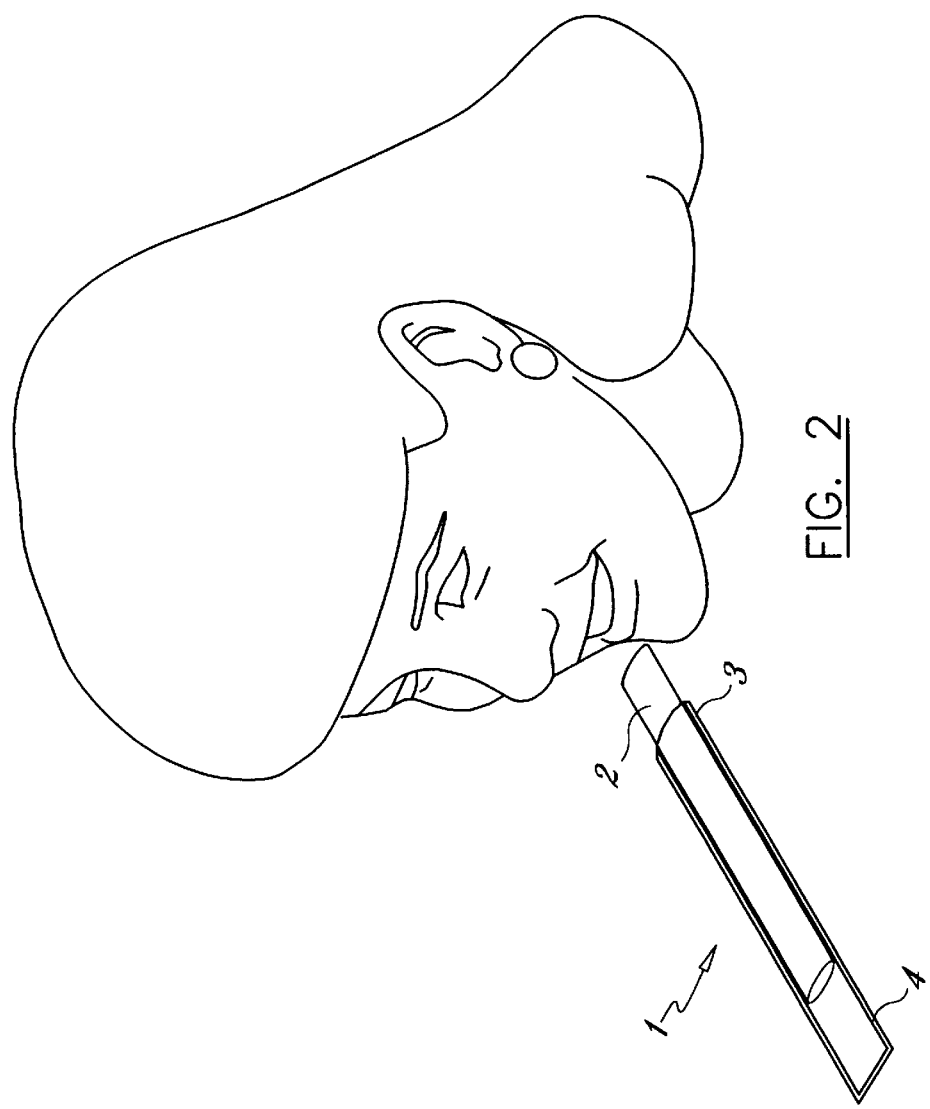
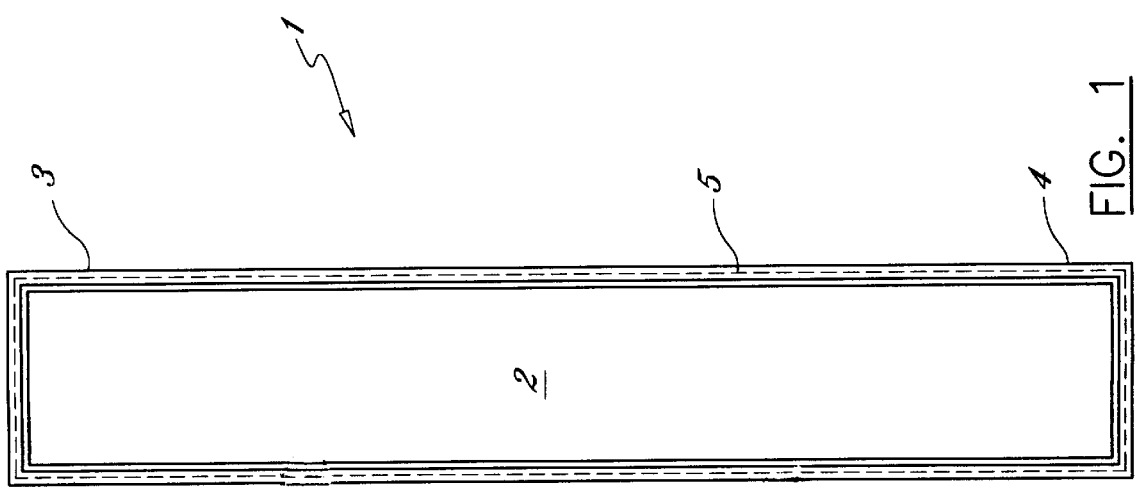

FROZEN AQUEOUS SOLUTION WITH NUTRIENTS METHOD OF PACKAGING AND UTILIZING THE SAME

BACKGROUND OF THE INVENTION

1. Field of the Invention

The field of the invention relates to nutritional supplements, foods, athletic dietary supplements, and frozen nutritional supplements.

2. Description of the Related Art

The traditional program for obtaining necessary vitamins and minerals is to attempt to eat a balanced diet and then to make up for the inevitable nutritional deficiencies by taking nutritional supplements and vitamin pills. However, for children, pill taking is difficult and sometimes impossible. So, instead of pills, liquid nutritional supplement solutions are offered. Unfortunately, children resist taking liquid supplements because they do not taste good. In addition, even if the liquid supplement tastes good, a child still may resist taking it because the child is stubborn and only will be "convinced" to take the supplement in a more attractive form.

The problem of pill taking is exasperated when the pill that the person is unable to take contains medicine. In some cases, liquid formulations are available. However, these syrups usually taste unpleasant. For these reasons, a good tasting means for taking medicine without pills is needed.

For athletes, nutritional supplements are typically packaged as sports drinks. Sports drinks help to replace fluids and electrolytes by containing water and nutrients. However, even when refrigerated, sports drinks are not able to cool the drinker sufficiently. In the case of a drink containing ice, the liquid is cooled to the freezing point but the liquid being consumed does not undergo a phase change inside the drinkers body. A phase change of solid to liquid (i.e., ice to water) absorbs significantly more heat than the heat transfer from the simple warming of a liquid.

In U.S. Pat. No. 5,780,451, DeMichele et al. discloses several nutritional compositions. In U.S. Pat. No. 4,021,583, Mehansho et al. describes a stable nutritional vitamin and mineral supplemented beverage. These compositions are not frozen. In addition, no method of ingesting the composition in a frozen state is described.

In U.S. Pat. No. 5,698,247, and U.S. Pat. No. 4,021,583, frozen confections and methods of making the same are disclosed. These confections are not nutritionally enriched.

In U.S. Pat. No. 4,218,482, Cook et al. discloses a Frozen, Nutritious Pet Food. This product is a frozen composition of one-third oil, one-third gas bubbles, and one-third nutrients. Cook's invention is not directed at being good tasting but rather satisfying the pet owner's desire to give the dog a treat that the owner would expect to be tasty because as the inventor states, "If the owner doesn't buy it, the pet doesn't get to eat it." (col 1, lines 67–8). In addition, the composition comprises ingredients for a dog; these ingredients even when combined with other teachings still produce a composition that is palatable to pets only. By not tasting good, people consuming the food would not want to hold it in their mouth and allow it to melt; the consumer would not be able to absorb the nutritional elements through the mucosal and sub-lingual membranes of the mouth. The pet food also is oil based. Oil based products contain calories and cholesterol and are not considered "health food." In addition, Cook does not disclose a method of consuming or packaging the composition to enable absorption through the mucosal membrane of the mouth. Nor does Cook disclose a method of using the frozen composition to cool the pet.

Frozen electrolyte compositions are available under the tradename PEDIALYTE®, a registered trademark of Ross Products Division, Abbott Laboratories, Inc., Columbus, Ohio. These freeze pops contain a solution containing electrolytes. The composition is designed to prevent dehydration particularly in infants. The PEDIALYTE® composition does not include active ingredients such as nutrients including carbohydrates, vitamins, minerals, and medicine.

SUMMARY OF THE INVENTION

The invention relates to a frozen comestible composition containing an active ingredient. For purposes of this invention, an active ingredient is a substance that has an effect on the taker.

The active ingredient can include a nutrient mixture. The nutrient mixture can include essential vitamins and minerals along with flavor agents which are other pleasant-tasting ingredients. Preferably, the composition is ingested like a popsicle or squeeze pop. The composition can be varied for different applications such as children, athletes, geriatric users, or infirm individuals.

The nutrients contained in the composition include vitamins and minerals. Specifically, these nutrients include Vitamin A, Vitamin C, Vitamin D, Vitamin E, Vitamin B1, Vitamin B2, Vitamin B6, Vitamin B12, Niacinamide, Pantothenic Acid, Paba, Choline, Inositol, Folic Acid, d-Biotin, Calcium, Magnesium, Iron, Manganese, Zinc, Potassium, Selenium and Iodine. The nutrients can also include nutritional energy sources such as carbohydrates.

To make the taste of the composition more palatable, flavor agents can be included in the composition.

To add the aesthetic attractiveness as well as to help a consumer identify the flavor, food coloring can be added to the composition.

Children prefer the frozen composition over other means of obtaining vitamins and nutrients because the composition contains flavors and sweeteners and because the composition, when frozen, resembles another favorite food, an ice pop.

For athletes, the invention provides a means to quickly absorb nutrients, replace fluids, and cool the user.

Infirm patients who have upset stomachs or lack of appetite may find the frozen composition to be a more attractive way to obtain nutrients.

The composition can include an active ingredient that is a medicine. These medicines include those available over the counter and those sold by prescription. By delivering medicine in a freeze pop, people who are unable to take pills are provided a means for taking medicine. Furthermore, when the composition includes flavors and sweeteners, the composition provides a tasty, enjoyable means for taking medicine. In addition, a sufficient dosage of the medicine can be included in each freeze pop. This dosage can be varied depending on the situation: for example, smaller for children, larger for adults.

For purposes of the invention, the mere inclusion of electrolytes is not to be considered an active ingredient. However, electrolytes can be an ingredient added in the product having active ingredients. Diarrhea and perspiring are two common causes for dehydration and loss of electrolytes. By consuming a frozen product containing additional electrolytes, fluid and electrolytes can be quickly replaced. In addition, by allowing the product to melt in the consumer's mouth, the electrolytes can be absorbed quickly through the consumer's oral mucosal glands. Oral absorption is especially significant in consumers who have diarrhea and other digestive disorders that prevent absorption in the stomach.

An object of the invention is to provide a tasty, good-textured composition containing nutrients such as vitamins and minerals.

Another object of the invention is to provide a means for children who are too young to take pills to ingest nutrients.

Another object of the invention is to provide a means for athletes to recover water and active ingredients including but not limited to nutrients such as carbohydrates, minerals, medicine, and electrolytes, while cooling themselves.

Another object of the invention is to provide an ice pop that is not only tasty but nutritious.

Another object of the invention is to provide a means to deliver a nutrient composition that can be absorbed through the mucosal and sub-lingual membranes of the mouth.

Another object of the invention is to provide a tasty means for taking a premeasured dosage of a medicine.

In accordance with these and other objects which will become apparent hereinafter, the instant invention will now be described with particular reference to the accompanying drawings.

BRIEF DESCRIPTION OF THE DRAWINGS

FIG. 1 is a top view of a frozen composition of nutrients held in a temporarily sealed bag.

FIG. 2 depicts a consumer who is in the process of extruding a frozen composition of nutrients from its unsealed plastic bag.

DETAILED DESCRIPTION OF THE PREFERRED EMBODIMENTS

The invention encompasses a composition of nutrients containing an active ingredient such as a nutrient mixture or a medicine. In its preferred embodiment, the chemical composition contains the following ingredients: active ingredients, flavoring agents, preservatives, food coloring, and a balance of water.

The composition contains an active ingredient. In a preferred embodiment, the active ingredients are a nutrient mixture. For purposes of this application, active ingredient is defined as a substance that has an effect on the taker. The nutrient composition contains vitamins and/or minerals that the body requires. The following table includes the ingredient, amount (where iu=international unit, mcg=microgram, mg—milligram), and percentage of recommended daily intake for children two to three years old taking one half a dose, and people four years and older taking a full dose. A dose is one and one-half fluid ounces (1½ oz).

| INGREDIENT | AMOUNT | % DAILY VALUE FOR CHILDREN 2–3 YEARS (½ DOSE) | % DAILY VALUE FOR 4 YEARS OLD AND OLDER (FULL DOSE) |
|---|---|---|---|
| Vitamin A | 5000 iu | 100 | 100 |
| Vitamin C | 150 mg | 120 | 100 |
| Vitamin D | 400 iu | 50 | 100 |

-continued

| INGREDIENT | AMOUNT | % DAILY VALUE FOR CHILDREN 2–3 YEARS (½ DOSE) | % DAILY VALUE FOR 4 YEARS OLD AND OLDER (FULL DOSE) |
|---|---|---|---|
| Vitamin E | 30 iu | 150 | 100 |
| Vitamin B1 | 5 mg | 166 | 333 |
| Vitamin B2 | 5 mg | 147 | 294 |
| Vitamin B6 | 5 mg | 125 | 250 |
| Vitamin B12 | 10 mcg | 83 | 167 |
| Niacinamide | 15 mg | 37 | 75 |
| Pantothenic Acid | 15 mg | 75 | 150 |
| Paba | 5 mg | n/a | n/a |
| Choline | 10 mg | n/a | n/a |
| Inositol | 10 mg | n/a | n/a |
| Folic acid | 100 mcg | 12 | 25 |
| d-Biotin | 50 mcg | 8.35 | 16.7 |
| Calcium | 25 mg | 1.2 | 2.5 |
| Magnesium | 12 mg | 1.5 | 3 |
| Iron | 5 mg | 11.5 | 23 |
| Manganese | 1 mg | n/a | n/a |
| Zinc | 2 mg | 6 | 12 |
| Potassium | 2 mg | n/a | n/a |
| Selenium | 5 mcg | n/a | n/a |
| Iodine | 0.05 mg | 16.5 | 33 |

The above formulation of the nutrient mixture is considered the best mode of providing the optimum dose of vitamins and nutrients to the consumer on a daily basis. The relative amounts and types of nutrients can be adjusted for specific individuals. More specifically, formulations can be made for consumers having different needs such as children, geriatric users, athletes, and infirm individuals.

The formulation including the vitamin complexes are preferably water-soluble.

In an alternate preferred embodiment, the active ingredient is a medicine. The medicine can be of the type sold over the counter or the type prescribed. The medicine can be organic or inorganic. Preferably, the amount of medicine in each freeze pop can be tailored to the proper dosage for the taker. For example, freeze pops for children would have a lesser dosage than freeze pops for adults.

The composition preferably contains at least one flavoring agent. These flavoring agents are flavors and sweeteners that include but are not limited to high fructose corn syrup, dextrose, sugar, five-percent fruit juice, pectin, citric acid, cellulose gum, natural flavors, artificial flavors, and sodium citrate. Flavoring agents are not required but are included for several reasons. First, the composition when frozen is to be held in the user's mouth and allowed to melt. By adding flavoring agents the composition is more palatable. Without flavoring agents, the user might be induced to swallow the composition to avoid the taste before the nutrients have had a full chance to absorb through the user's mucosal and sub-lingual membranes. The amounts of these ingredients can also be adjusted to enhance the texture and freezing qualities of the composition.

The composition preferably contains preservatives. The preservatives include but are not limited to sodium benzoate and potassium sorbate. Although not required, preservatives are included in the composition to extend the shelf life of the composition and to prevent spoilage.

The composition preferably contain food colorings. These food colorings include but are not limited to U.S. Certified Food Colors Red #40, Yellow #6, and Blue #1. Although not required, food colorings are included to enhance the aesthetic desirability of the composition. Food coloring also helps consumers associate the color with the flavor. For example, strawberry flavor can be died red and blueberry flavor might be died blue.

The balance of the composition is water. Water is added to dilute the other ingredients to their preferred concentrations. By adding a substantial percentage of water, the freezing point of the composition is approximately the same as water. This allows conventional freezing techniques to be used and it allows for a predictable melting of the composition during consumption. The term "balance of the composition" is not to be read to limit the inclusion of other ingredients besides those specifically claimed.

In its preferred form, the above-described composition is frozen. To make a frozen composition of nutrients, the composition is placed in an environment below its freezing point for a time long enough to allow the composition to freeze.

Looking at FIG. 1, a preferred method of preparing the composition for consumption includes packaging the composition in a releasably-sealable, long, slender, plastic package, generally marked 1. According to this method, composition 2 is inserted inside bag 1 and bag 1 is sealed around perimeter 5. Composition 2 can be packaged as a liquid or a frozen solid. In either case, the consumer would place bag 1 containing the liquid into a freezer (not shown) thereby freezing composition 2. Composition 2 remains in the freezer until the time composition 2 is to be consumed. Plastic bags have the advantage of not bursting even when composition 2 comprised mainly of water expands during freezing. To consume frozen composition 2, first end 3 of bag 1 is opened and frozen composition 2 is extended by pressing second end 4 that opposes first end 3.

When ingesting the frozen composition, the frozen composition is to be put in the consumer's mouth and allowed to melt. After the composition has melted, the consumer can swallow the composition. By consuming the composition in such a manner, the composition remains in the consumer's mouth for an extended period of time where it can be absorbed into the consumer's body through the user's oral mucosal membranes and sub-lingual membranes. The composition continues to be absorbed by the consumer's digestive system after swallowing.

For athletes, the frozen composition provides the additional benefit of cooling the athlete as the composition melts. The cooling can be combined with a composition containing enhanced amounts of electrolytes which are routinely lost during exercise when the athlete perspires. While electrolytes may be included, for purposes of this invention, electrolytes by themselves are not to be considered an active ingredient.

For infirm patents who have upset stomachs or lack of appetite, the frozen composition provides the patients with a way to absorb nutrients that does not rely on the patient swallowing the composition.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. An enhanced frozen comestible product for providing nutritional supplements making them more palatable for children consisting of:

an active ingredient in addition to any electrolytes, and the balance of water;

wherein said active ingredient is a nutrient mixture consisting of vitamin A, vitamin C, vitamin D, vitamin E, vitamin B1, vitamin B6, vitamin B12, niacinamide, pantothenic acid, paba, choline inositol folic acid, d-biotin calcium, magnesium, iron, manganese, zinc, potassium, selenium, iodine; and at least one flavoring agent, said flavor agent being chosen from the group consisting of high fructose corn syrupy dextrose, sugar, five percent fruit juice, pectin, citric acids cellulose gum, natural flavors, artificial flavors, and sodium citrate.

2. The composition as described in claim 1 further comprising a preservative.

3. The composition as described in claim 1, wherein said preservative is chosen from the group consisting of sodium benzoate and potassium sorbate.

4. A composition as described in claim 1 further comprising a food coloring.

5. A composition as described in claim 1, wherein said food coloring is chosen from the group consisting of U.S. Certified Food Colors Red #40, Yellow #6, and Blue #1.

6. A composition as described in claim 1, further comprising carbohydrates.

7. A nutritional supply system for providing vitamins, minerals and other nutrients for children in order to make the nutrients more palatable for children comprising:

a sealable plastic container that includes the composition of water and nutrient supplements consisting of vitamin A, vitamin C, vitamin D, vitamin E, vitamin B1, vitamin B6, vitamin B12, niacinamide, pantothenic acid, paba, choline inositol folic acid, d-biotin, calcium, magnesium, iron, manganese, zinc, potassium, selenium and iodine to form a freezable liquid inside said sealable container, said freezable liquid also including a flavoring agent for making the composition more palatable for children that is chosen from a group consisting of high fructose corn syrup, dextrose, sugar, five percent fruit juice, pectin, citric acid, cellulose gum, natural flavors, artificial flavors, and sodium citrate.

* * * * *